United States Patent [19]
Newby et al.

[11] Patent Number: 6,017,317
[45] Date of Patent: Jan. 25, 2000

[54] ASSEMBLY FOR COLLECTING BLOOD OR OTHER BODY FLUIDS

[75] Inventors: C. Mark Newby, Tuxedo, N.Y.; Henry F. Miller, Clifton, N.J.; Keith E. Schleiffer, Gahanna, Ohio

[73] Assignee: Becton Dickinson and Company, Franklin Lakes, N.J.

[21] Appl. No.: 08/955,352

[22] Filed: Oct. 21, 1997

Related U.S. Application Data

[60] Provisional application No. 60/042,062, Mar. 26, 1997.

[51] Int. Cl.$^7$ .................................................. A61B 5/00
[52] U.S. Cl. ........................ 600/573; 215/247; 604/403; 604/415; 600/576
[58] Field of Search .................... 215/247, 341; 604/403, 415; 600/573, 576, 577

[56] References Cited

U.S. PATENT DOCUMENTS

| | | | |
|---|---|---|---|
| 4,967,919 | 11/1990 | Earhart | 215/247 |
| 5,033,476 | 7/1991 | Kasai | 600/577 |
| 5,061,263 | 10/1991 | Yamazaki et al. | 604/403 |
| 5,232,111 | 8/1993 | Burns | 215/320 |
| 5,275,299 | 1/1994 | Konrad et al. | 215/341 |
| 5,297,561 | 3/1994 | Hulon | 600/577 |
| 5,433,716 | 7/1995 | Leopardi et al. | 604/415 |
| 5,494,170 | 2/1996 | Burns | 216/247 |
| 5,632,396 | 5/1997 | Burns | 215/247 |

*Primary Examiner*—Cary O'Connor
*Assistant Examiner*—Charles Marmor, II
*Attorney, Agent, or Firm*—Nanette S. Thomas, Esq.

[57] ABSTRACT

An assembly for collecting blood or other body fluids is provided. The assembly includes an elongate tube having an open end and a closed end. The open end includes threads. An internally threaded plastic cap is mounted to the open end of the tube. The cap includes an axial passage and a resealable member aligned with the axial passage. A gas-impermeable member is bonded to the resealable member and the open end of the tube. Both the resealable member and gas-impermeable member are pierceable by a needle. The cap is removable with the resealable member and the gas-impermeable member as a unit due to the fact that the bond between the gas-impermeable member and the tube is weaker than that between the gas-impermeable member and the resealable member. The cap includes a deflectable portion near its top end to engage the walls of a tube holder, and to function as a shock absorber if the tube is dropped.

19 Claims, 8 Drawing Sheets

ASSEMBLY FOR COLLECTING BLOOD OR OTHER BODY FLUIDS

This application claims Benefit of Provisional Application No. 60/042,062 filed Mar. 26, 1997.

BACKGROUND OF THE INVENTION

1. Field of the Invention

The field of the invention relates to assemblies for collecting blood or other body fluids, the assemblies being of the type including a container having a closure assembly pierceable by a needle or cannula.

2. Description of the Related Art

Blood collection tubes are commonly used by doctors, nurses and other persons to draw a sample of a body fluid from a patient or to receive a fluid sample from another vessel. Such tubes are ordinarily evacuated, and include a pierceable closure. During one typical use of a blood collection tube, one end of a double-ended needle assembly is used to pierce a vein. The evacuated blood collection tube is then urged towards the second end of the double-ended needle assembly until its closure is pierced. Blood is thereby drawn into the tube.

The double-ended needle assembly is ordinarily mounted to a holder having a tubular body. The blood collection tube is inserted within the tubular body in order to engage the second end of the double-ended needle assembly.

The maintenance of a vacuum within the blood collection tube is important. Blood collection tubes may be stored for considerable lengths of time before they are used. Loss of vacuum during storage or at any time can render the collection tube less effective or useless.

A number of designs of blood collection tubes and their closures have been the subjects of patents and other disclosures. British Patent Specification 1 388 494 and U.S. Pat. No. 4,327,746 both disclose closures for such tubes having sealing membranes positioned between a cap and the open end of the collection tube. U.S. Pat. No. 5,061,263 discloses several closure designs, each including a cap, a gas barrier member and a re-sealable member.

U.S. Pat. Nos. 4,150,666, 4,967,919, 4,991,601, 5,326,534, 5,494,170 and International Publication No. WO 81/01238 disclose various blood collection tubes and/or holders for such tubes. The '170 patent discloses a cap having flexible tabs which engage the wall of the holder, thereby maintaining the blood collection tube within the holder.

SUMMARY OF THE INVENTION

The present invention provides a body fluid collection assembly which is capable of maintaining a vacuum for an extended period of time, is easily penetrable by a needle, and which includes a closure assembly that is both easily removed and easily reinstalled. A novel closure assembly for a body fluid collection tube is also provided.

An assembly in accordance with the invention includes an elongate, generally cylindrical container having a closed end and an open end. A closure assembly is removably mounted to the open end of the container, preferably by interengaging threads. The closure assembly includes a cap and a resealable member secured to the cap. The cap includes an opening for permitting access to the interior of the container. The resealable member covers this opening. A gas barrier member, which may be comprised of a metal foil, is bonded to the open end of the container and to the closure assembly. The bond between the gas barrier member and container is weaker than that between the gas barrier member and closure assembly. This allows the gas barrier member to be removed with the closure assembly from the open end of the container without suffering appreciable damage. Both the resealable member and gas barrier member are penetrable by a needle the resealable member providing a substantially liquid-impermeable seal upon withdrawal of the needle.

The cap of the invention preferably includes a deflectable portion at the top end thereof. The deflectable portion should be designed to engage a planar surface if the container is placed horizontally on such a surface. This allows the deflectable portion to function as a shock absorbing system which will help preserve the bond between the gas barrier and the container should the container be dropped. It also provides a superior interference fit when the container is inserted within a tube holder.

The open end of the container preferably includes external, interrupted threads. The cap preferably includes a plurality of internal threads, each of which includes a lead portion. Internal tabs are provided adjacent each of the lead portions for allowing the user to easily locate the cap for reapplication to the open end of the container. The threads preferably allows the cap to be removed upon less than 180° rotation so that such removal can be accomplished using only one hand.

DETAILED DESCRIPTION OF THE INVENTION

Figure 1:
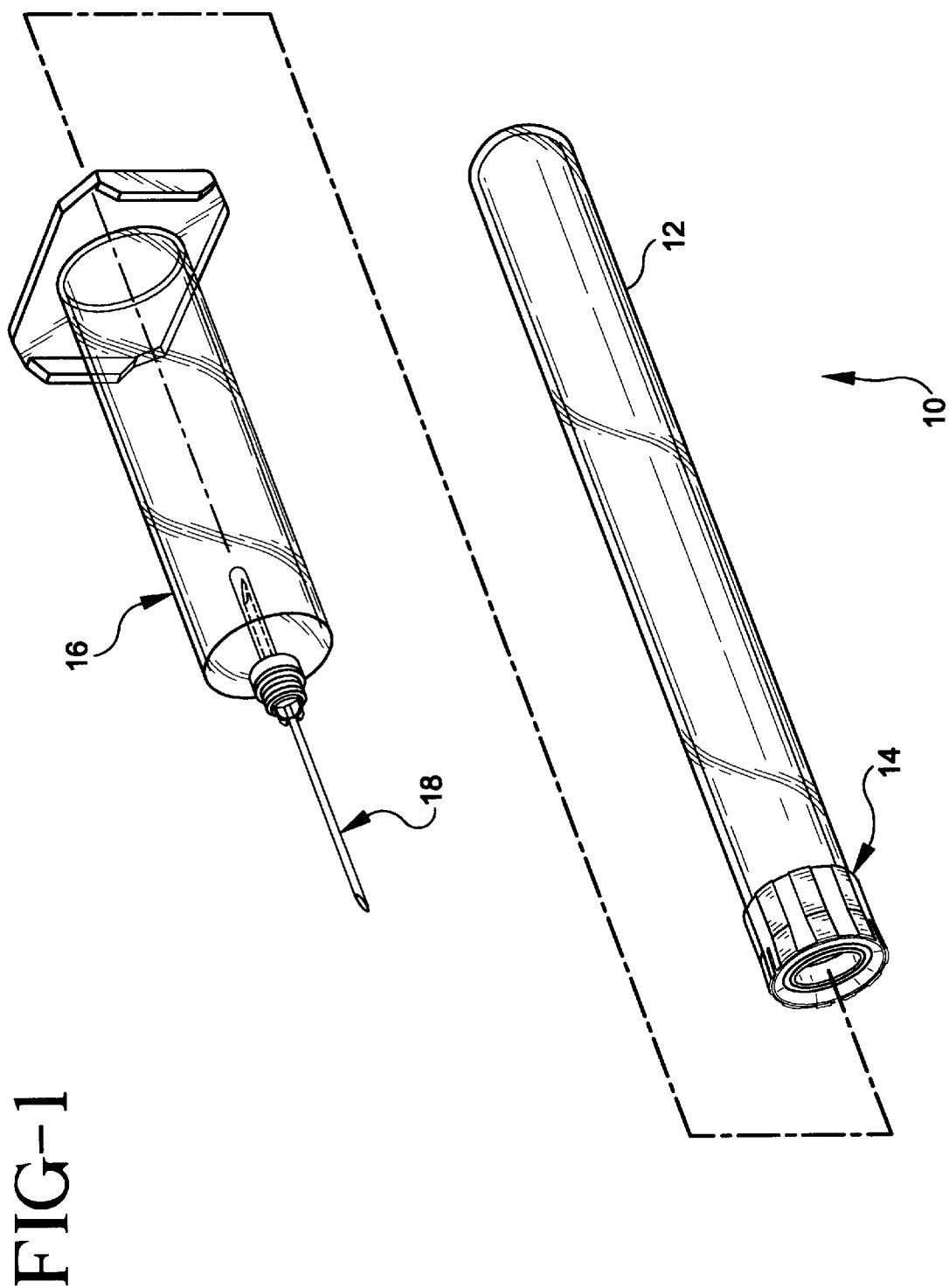
FIG. 1 is a perspective view of an assembly for collecting body fluids and a tube holder capable of receiving a portion of the assembly.
Figure 2:
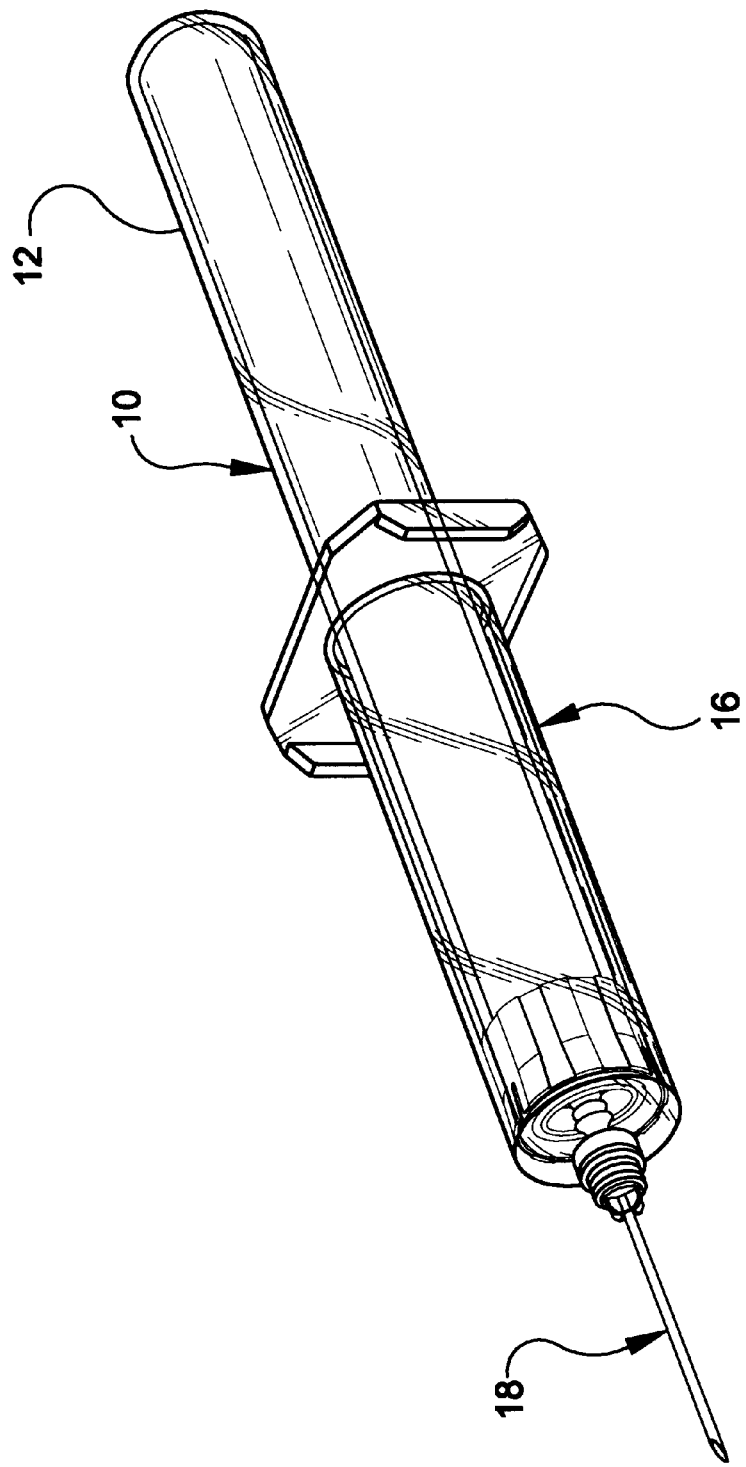
FIG. 2 is a top perspective view showing the assembly having an end portion positioned within the tube holder.

An assembly 10 for collecting blood or other body fluids is provided by the invention. Referring to FIGS. 1–6, the assembly includes a generally cylindrical container 12 having a closed end and an open end, and a closure assembly 14 which can be removably mounted to the open end of the container. As shown in FIGS. 1–5, the container may be employed in conjunction with a holder 16 to which a double-ended needle assembly 18 is mounted.

Figure 6:
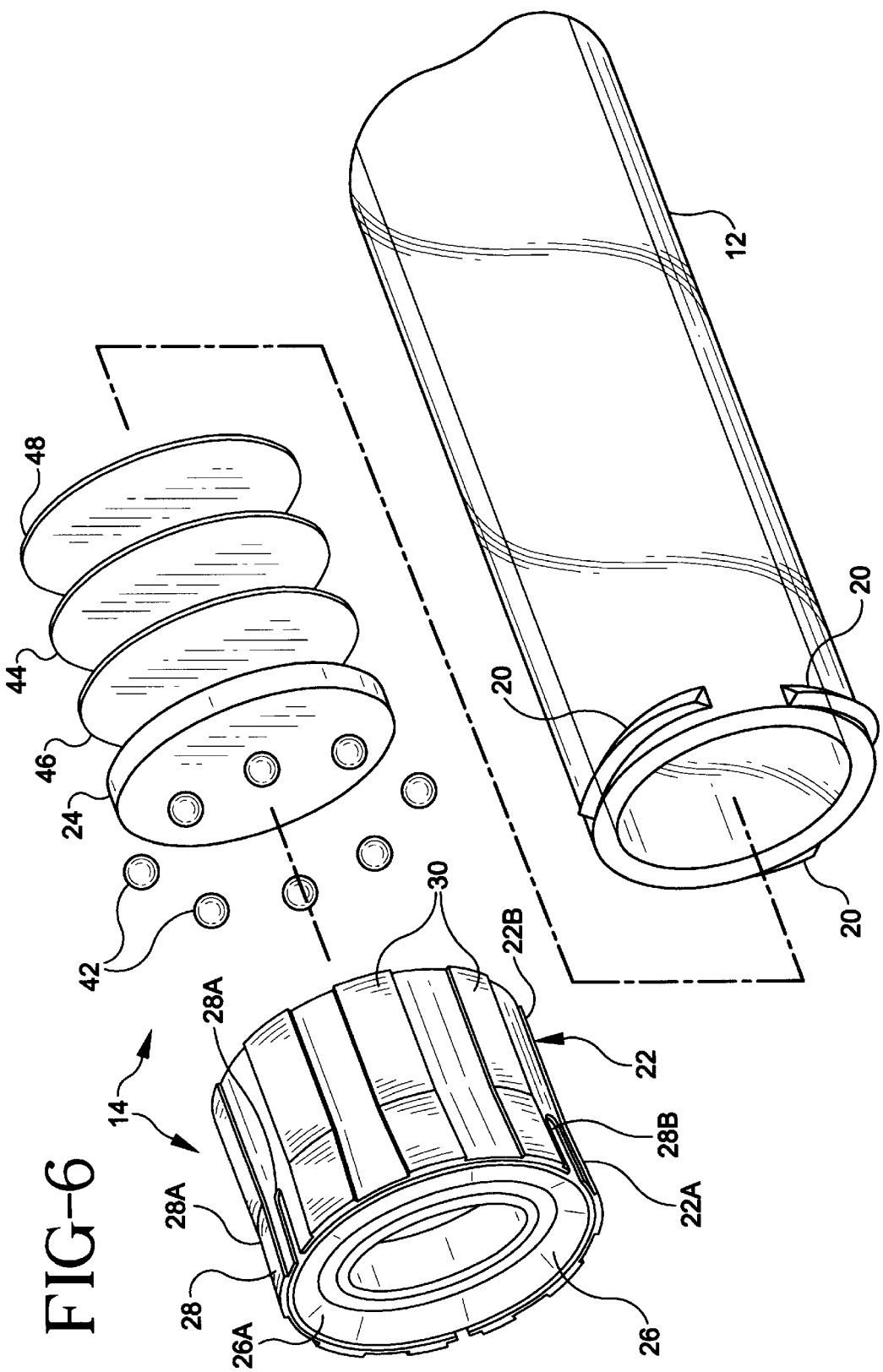
FIG. 6 is an exploded, perspective view of the assembly for collecting body fluids.
Figure 7:
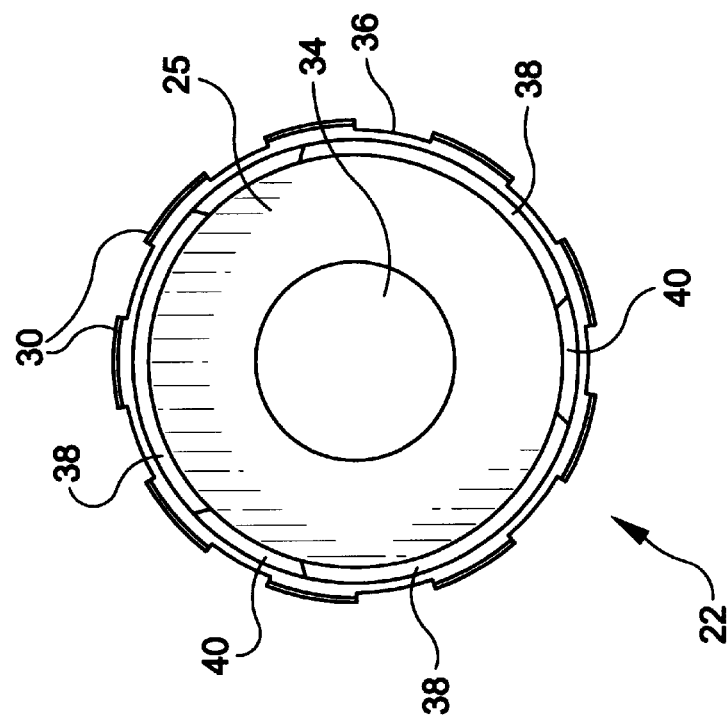
FIG. 7 is a top plan view of a cap of the assembly for collecting body fluids.
Figure 8:
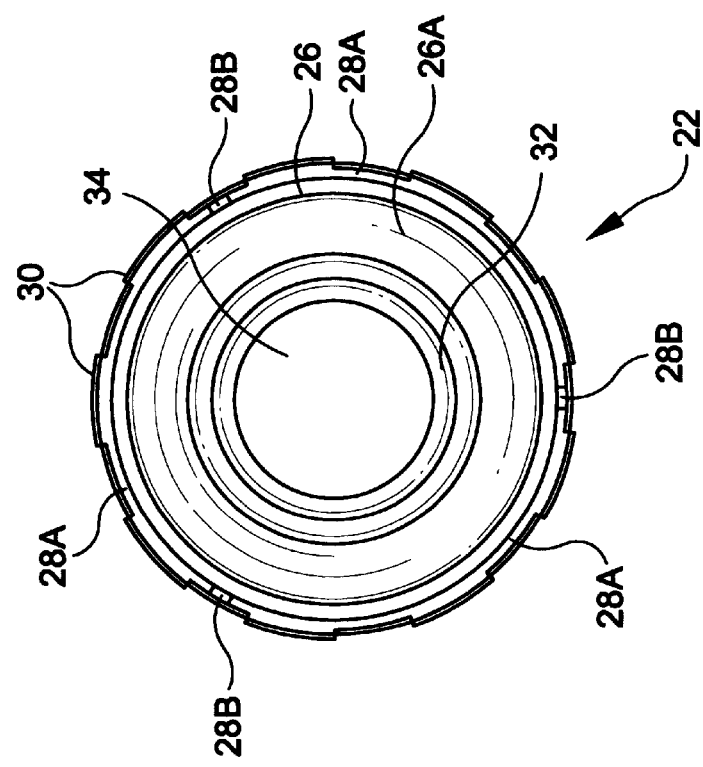
FIG. 8 is a bottom plan view of the cap of FIG. 7.

The container 12 is preferably transparent, and is preferably made from a material that is substantially gas-impermeable, such as glass or polyethylene terephthalate (PET). As shown in FIG. 6, the container includes an interrupted thread including three thread segments 20. Each thread segment has a first end portion adjoining the rim and a second end portion displaced spirally downwardly with respect to the first end portion. A gap separates each thread segment. The depth of the interrupted thread shown in the drawings is less than about 0.070 inches.

Figure 5:
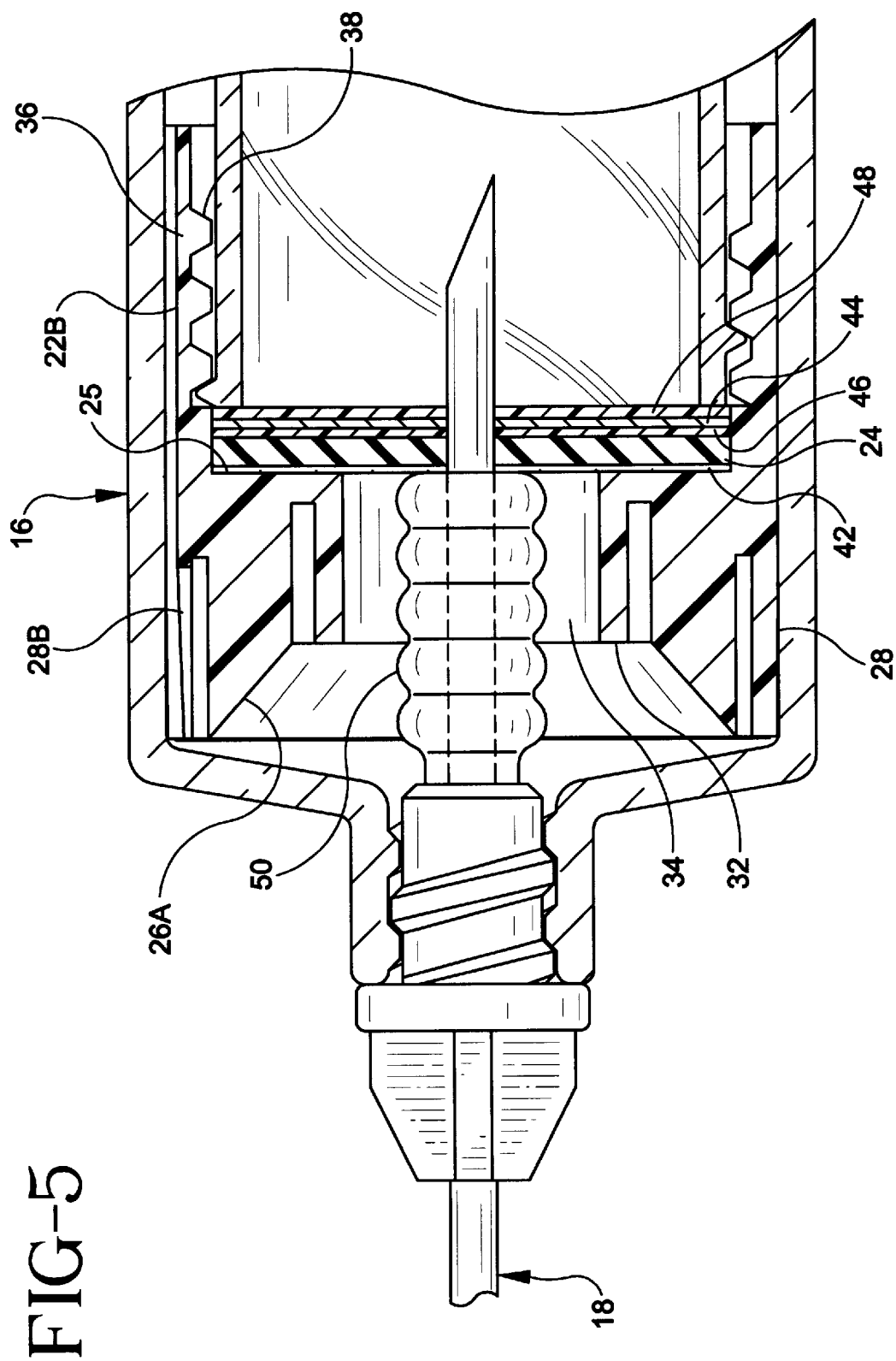
FIG. 5 is an enlarged, sectional view showing the assembly fully inserted within the tube holder.

The closure assembly 14 is most clearly illustrated in FIGS. 5 and 6. It includes a generally cylindrical cap 22 made of polypropylene or other semi-rigid polyolefin material and a resealable member 24. The resealable member is made from an elastomeric material such as polyurethane or, alternatively, butyl rubber, which is capable of resealing itself following piercing of the same by a needle and subsequent needle withdrawal.

The cap 22 includes a top portion 22A and a bottom portion 22B. An annular shoulder 25 is defined by the bottom surface of the top portion of the cap. The top portion of the cap further includes an annular, substantially rigid body portion 26 surrounded by an annular deflectable portion 28. The deflectable portion 28 is comprised of a plurality of arcuate walls 28A separated by slots 28B extending downwardly from the upper rim of the deflectable portion. The outer surface of the cap includes a plurality of elongate, radially extending protrusions 30. These protrusions facilitate the handling of the cap and assembly 10. They also provide contact surfaces in the event the assembly is dropped. Force is thereby imparted to the deflectable portion 28 of the cap.

The body portion 26 of the upper portion of the cap includes a chamfered upper surface 26A, which may include indicia such as opening and closing instructions. An annular wall 32 is positioned inwardly of the body portion 26. The inner surface of this annular wall 32 defines an axial opening 34 extending through the upper portion of the cap.

Figure 9:
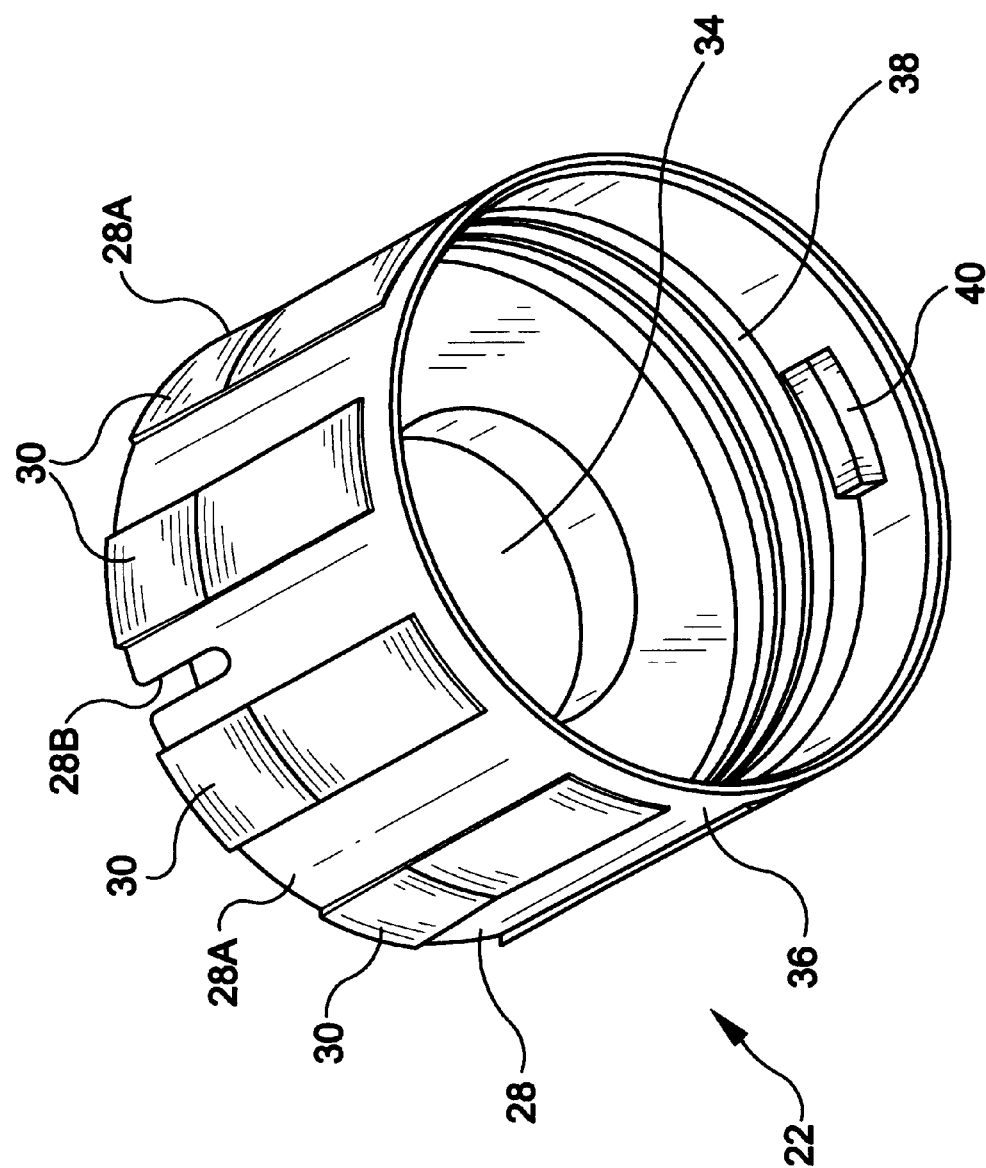
FIG. 9 is a bottom perspective view of the cap of FIG. 7.

The bottom portion 22B of the cap 22 is defined by a substantially cylindrical wall 36 including a plurality of internal threads 38. In the embodiment shown herein, three spiral threads are provided, each having a thread lead adjoining a locating tab 40. (See FIG. 9). The locating tabs extend axially towards the bottom of the cap. The width of each tab is smaller than the width of each gap which separates the external thread segments 20 of the container 12. Each thread 38 extends spirally for 180° or less, preferably about 120–140°. This allows the cap 22 to be mounted to or removed from the container by turning it 180° or less. Such a task does not ordinarily require a two-handed operation. The cap can alternatively be snapped on the container. This feature facilitates the manufacturing process. The locating tabs facilitate rethreading the cap onto the container subsequent to its initial removal.

The resealable member 24 is shown in the drawings as a flat disc. This particular configuration is not critical, though a relatively thin center portion does facilitate needle penetration. The member 24 is secured to the shoulder 25, thereby closing the opening 34 through the upper portion of the cap 22. Hot melt adhesive 42 or other suitable adhesive may be used to permanently secure the resealable member to the cap.

A gas barrier member 44 is secured to the resealable member 24 by a tie layer 46 of adhesive material or a material such as PET. The gas barrier member is also bonded to the top portion of the container, and preferably the rim, by a seal layer 48 which may also be PET. (See FIGS. 5 and 6). A seal layer which allows induction sealing is preferred. It should be understood that the drawings of the resealable member, gas barrier member and other sealing members are not to scale. The gas barrier member is preferably a metal foil, such as aluminum foil, having a thickness of about 0.001 inch. The tie and seal layers 46, 48 may be coatings on the gas barrier member.

Figure 4:
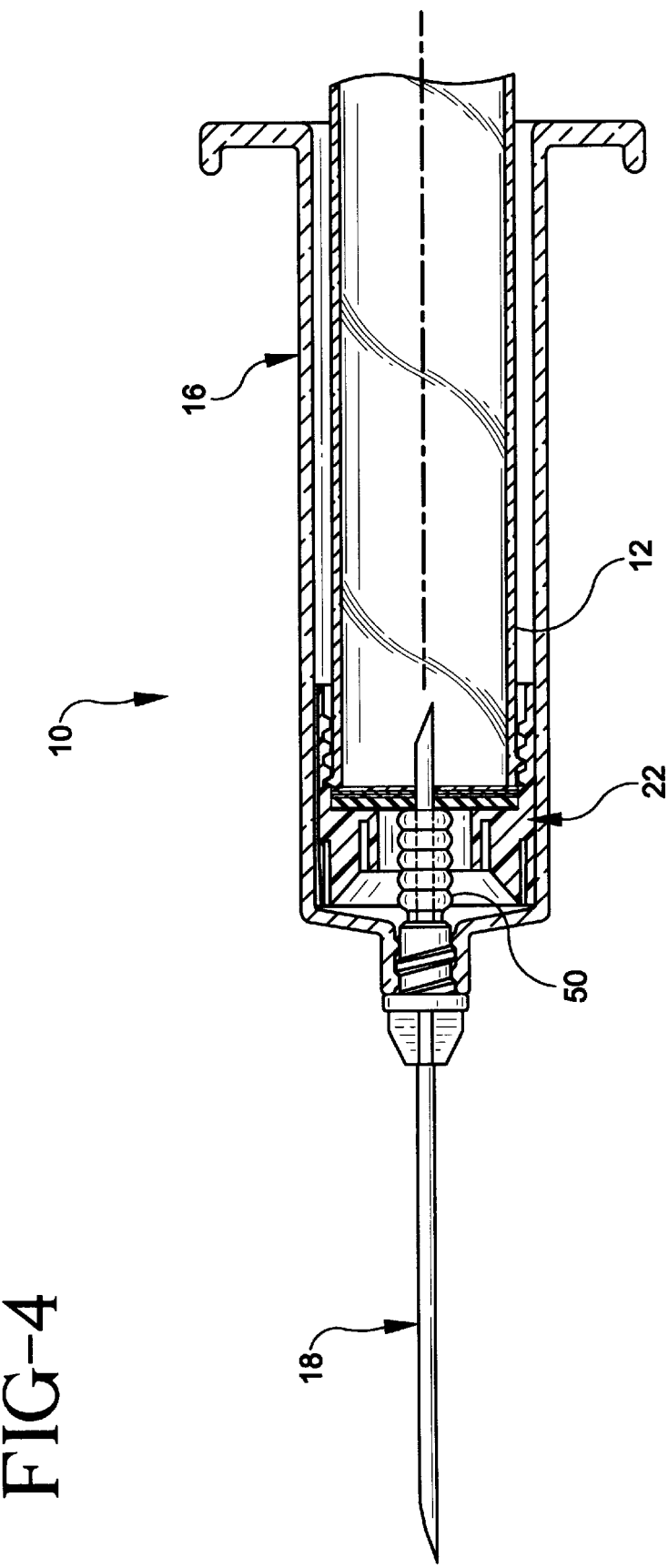
FIG. 4 is a sectional elevation view showing the assembly positioned within the tube holder.

The assembly 10 as described above may be used with a holder 16 as shown in the drawings or other holders known to the art. As shown in FIG. 4, the assembly 10 is used to collect blood or other body fluid when inserted within the holder such that the rear end of the double-ended needle assembly 18 extends through the resealable member 24 and gas barrier member 44. The figures show a sheath 50 which is displaced upon insertion of the assembly 10 into the holder. The use of such a sheath is not required.

Figure 3:
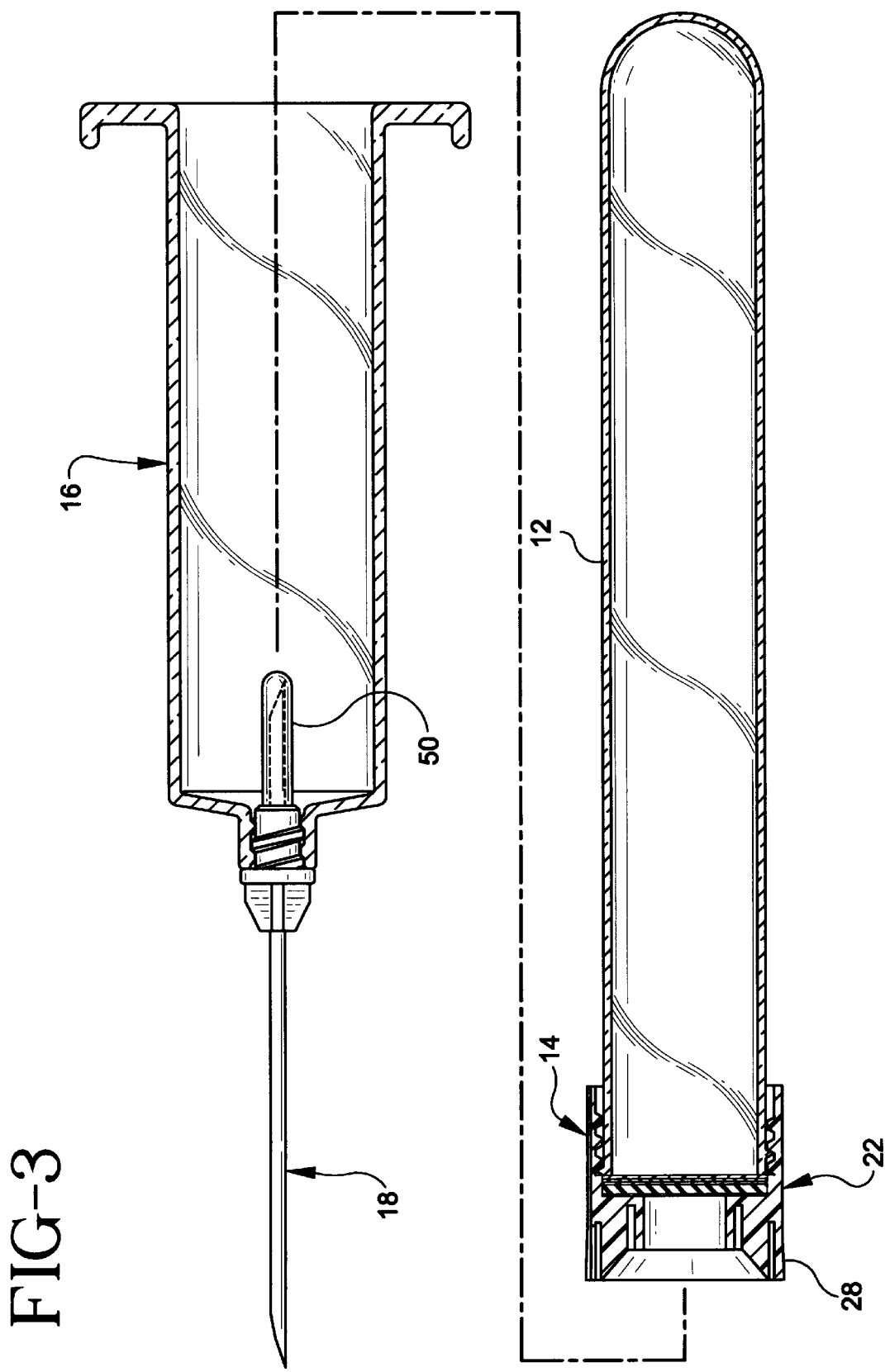
FIG. 3 is a sectional elevation view showing the assembly for collecting body fluids and the tube holder.

The assembly 10 is provided to users in the form shown in FIGS. 1 and 3. The container 12 is ordinarily at least partially evacuated. As discussed above, the assembly 10 is designed to maintain a desired vacuum for a considerable length of time. The product should accordingly have a satisfactory shelf life.

Once the fluid collection procedure is completed, the assembly 10 is withdrawn from the holder 16. Though the closure assembly 14 is no longer gas-impermeable following such withdrawal, liquid impermeability is maintained by the resealable member. The assembly 10 can then be transported to an area where the fluid content of the container can be analyzed.

Removal of the closure assembly 14 is a relatively simple procedure which can be accomplished with one hand. The cap 22 is rotated about 120–140° in accordance with the preferred embodiment of the invention, and is then moved away from the open end of the container. The contents of the container can then be accessed. The closure assembly can be secured again to the open end of the container by first placing the cap over this end and then rotating it. The locating tabs 40 greatly facilitate the engagement of the container threads 20 and the cap threads 38.

Because the seal between the gas barrier member 44 and the container is relatively weak, this element preferably suffers no damage as the cap is turned and ultimately removed. The cap, resealable member and gas barrier member are accordingly removed as a unit and reapplied as a unit. The gas barrier member, being intact, forms a liquid-tight seal with the top rim of the container when the closure assembly is reapplied.

While the invention has been described with respect to the preferred embodiment thereof, it will be appreciated that alternative approaches may be taken with respect to the structures of the cap, sealing elements, and container. The threads employed for engaging the cap and container could, for example, be replaced by other engagement structures such as a bayonet locking arrangement (not shown).

It should be understood that the above-described embodiment of the present invention is simply illustrative of the preferred embodiment thereof. Variations of such embodiment, including those discussed above and others, could be made to or used in the embodiment disclosed and still remain within the scope of the present invention.

What is claimed is:

1. An assembly for collecting blood or other body liquids, comprising:
    an elongate, cylindrical container having a closed end and an open end;
    a closure assembly removably mounted to said open end of said container, said closure assembly including a cap and a resealable member;
    said cap having an opening for permitting access to the interior of said container, said resealable member being secured to said cap and covering said opening;
    a gas barrier member covering said open end of said container and being secured to said open end of said container by a first means for bonding and secured to said resealable member by a second means for bonding, whereby said first means for bonding between said gas barrier member and said container being weaker than said second means for bonding between said gas barrier member and said resealable member such that said gas barrier member is removable with said cap and resealable member upon removal of said cap from said open end of said container without being damaged as the bond between said gas barrier member and said open end of said container is broken;

both said resealable member and said gas barrier member being penetrable by a needle, said resealable member providing a liquid-impermeable seal upon withdrawal of the needle.

2. An assembly as described in claim 1, wherein said cap includes a top wall defining said opening, and said resealable member is bonded to the lower surface of said top wall of said cap.

3. An assembly as described in claim 2, wherein said gas barrier member is a metal foil adhered to said resealable member.

4. An assembly as described in claim 3, wherein said barrier member is bonded to a rim defining said open end of said container.

5. An assembly as described in claim 4, wherein said resealable member is an elastomeric disc, said metal foil and said elastomeric disc each including edge portions positioned between said rim of said container and said top wall of said cap.

6. An assembly as described in claim 1, wherein said cap includes at least one deflectable portion defining an outer surface of said cap.

7. An assembly as described in claim 6, wherein said cap includes a body portion, said deflectable portion being connected to said body portion and defining a generally cylindrical enclosure about the body portion of said cap.

8. An assembly as described in claim 6, including a tube holder comprising a housing and a needle coupled to said housing, said container being positioned at least partially within said housing, said deflectable portion of said cap engaging a wall of said housing and frictionally maintaining said container in a selected portion.

9. An assembly as described in claim 8 including a locating tab adjoining each of said thread leads of said cap.

10. An assembly as described in claim 1, wherein said container includes an external, interrupted thread adjoining said open end, said cap including an internally threaded surface including a plurality of thread leads.

11. An assembly as described in claim 1, wherein said container is substantially evacuated.

12. An assembly for collecting blood or other body fluid, comprising:

an elongate, generally cylindrical container having an open end and a closed end;

a closure assembly removably mounted to said open end of said container, said closure assembly including a cap having a top and bottom, a resealable member mounted to said cap, and an opening in said cap, said resealable member being aligned with said opening;

said cap including a deflectable portion at the top of said cap and defining an outer surface of said cap;

and a gas barrier member bonded to said open end of said container by a means for bonding; said gas barrier member also being bonded to said resealable member by a means for bonding, said resealable member being bonded to said cap, the means for bonding between said gas barrier member and said open end of said container being weaker than the means for bonding between said gas barrier member and said resealable member.

13. An assembly as described in claim 12, wherein said deflectable portion is comprised of a plurality of deflectable members.

14. An assembly as described in claim 13, wherein said deflectable members define a generally cylindrical outer wall of said cap.

15. An assembly as described in claim 14, including a plurality of axially extending slots defined within said generally cylindrical outer wall and separating said deflectable members.

16. An assembly as described in claim 14, wherein said cap includes a generally cylindrical body portion, said generally cylindrical wall being separated from said body portion by a substantially annular slot.

17. An assembly as described in claim 12, wherein said deflectable portion is an integral part of said cap.

18. An assembly as described in claim 12 including a tube holder comprising a housing and a needle coupled to said housing, said container being at least partially insertable into said housing such that said needle penetrates said resealable member and said deformable portion of said cap engages a wall of said housing, thereby frictionally maintaining said container in a selected position within said housing.

19. An assembly as described in claim 12, wherein said container is substantially evacuated.

* * * * *